United States Patent [19]

Chen et al.

[11] Patent Number: 5,221,625
[45] Date of Patent: Jun. 22, 1993

[54] CYCLCIC FR-900520 MICROBIAL BIOTRANSFORMATION AGENT

[75] Inventors: Shieh-Shung T. Chen, Morganville; Raymond F. White, Englishtown; Georgette Dezeny, Short Hills; Brian R. Petuch, Florence; George M. Garrity, Westfield; Byron H. Arison, Watchung; Amy M. Bernick, Glen Gardner, all of N.J.

[73] Assignee: Merck & Co., Inc., Rahway, N.J.

[21] Appl. No.: 818,936

[22] Filed: Jan. 10, 1992

[51] Int. Cl.$^5$ .......................... C12P 17/16; C12R 1/56
[52] U.S. Cl. ................................. 435/253.5; 435/118; 435/899
[58] Field of Search ............................ 435/899, 253.5

[56] References Cited

U.S. PATENT DOCUMENTS

| | | |
|---|---|---|
| 3,244,592 | 4/1966 | Arai . |
| 4,081,531 | 3/1978 | Arai et al. ............................ 435/899 |
| 4,242,453 | 12/1980 | Umezawa et al. ................... 435/899 |
| 4,264,607 | 4/1981 | Dewey et al. ........................ 435/899 |
| 4,894,344 | 1/1990 | Sugiyama et al. ................... 435/899 |

FOREIGN PATENT DOCUMENTS

| | | |
|---|---|---|
| 0184162 | 6/1986 | European Pat. Off. . |
| 0349049 | 6/1986 | European Pat. Off. . |
| 0349061 | 1/1990 | European Pat. Off. . |
| 0388152 | 9/1990 | European Pat. Off. . |
| 0388153 | 9/1990 | European Pat. Off. . |
| WO 89/05304 | 6/1989 | PCT Int'l Appl. . |
| 715362 | 9/1954 | United Kingdom ................ 435/899 |
| 1060444 | 3/1967 | United Kingdom ................ 435/899 |

OTHER PUBLICATIONS

"Catalogue of Bacteria and Phage" 17th ed. ATCC Ed. Gherna et al. 1989 p. 228 *S. lavendulae.*
J. Antibiotics A15, pp. 231–232, by Arai Jul. 31, 1962.

*Primary Examiner*—Herbert J. Lilling
*Attorney, Agent, or Firm*—Charles M. Caruso; Robert J. North; J. Eric Thies

[57] ABSTRACT

Described is a process for producing a new immunosuppressant, a C-19/C-22 cyclic hemiketal (Compound I) biotransformation analog of FR-900520, under novel fermentation conditions utilizing the novel microorganism, Streptomyces sp. (Merck Culture Collection MA6963) ATCC No. 55230. The macrolide immunosuppressant is useful in preventing human host rejection of foreign organ transplants, e.g. bone marrow, liver, lung, kidney and heart transplants.

1 Claim, 2 Drawing Sheets

CYCLCIC FR-900520 MICROBIAL BIOTRANSFORMATION AGENT

BACKGROUND OF THE INVENTION

1. Field of the Invention this invention relates to a new FK-506 type immunosuppressant agent, a C-19/C-23 cyclic hemiketal biotransformation analog of FR-900520 (Compound I), a novel fermentation process for its production, utilizing the novel microorganism Streptomyces sp. (MA6963), ATCC No. 55230. The process involves culturing the microorganism in the presence of FR-900520 under conditions which effect the biotransformation of FR-900520. Also disclosed is a method of its use in a human host for treatment of autoimmune diseases, infectious diseases and/or prevention of organ transplant rejections.

2. Brief Description of Disclosures in the Art

In 1983, the U.S. FDA approved cyclosporin, and extremely effective anti-rejection drug that revolutionized the field of organ transplant surgery. The drug acts by inhibiting the body's immune system from mobilizing its vast arsenal of natural protecting agents to reject the transplant's foreign protein.

As effective as the drug is in fighting transplantation rejection, it suffers drawbacks in causing kidney failure, liver damage and ulcers which in many cases can be very severe.

EPO Publication No. 0184162 to Fujisawa, hereby incorporated by reference, describes a new macrolide immunosuppressant FK-506 which is reputed to be 100 times more effective than cyclosporin. The macrolide is produced by fermentation of a particular strain of *Streptomyces tsukabaensis*. Also described is the closely related macrolide immunosuppressant FR-900520, produced by *S. hygroscopicus* subsp. vakushimaensis.

T. Arai U.S. Pat. No. 3,244,592 describes the culturing of *Streptomyces hygroscopicus* var. ascomyceticus to produce the antifungal "ascomycin", which has been shown to be the same compound as FR-900520.

There is, however, no description in the literature of the production of any FK-506 type immunosuppressive agents, which substantially lack the side effects or similar side effects to cyclosporin.

In this regard, new FK-506 type immunosuppressants are continuously being searched for.

SUMMARY OF THE INVENTION

It has been found that a new FK-506 type immunosuppressant, Compound I, can be obtained by the fermentation of the microorganism Actinomycete (MA6963), ATCC No. 55230, together with the macrolide immunosuppressant FR-900520, under submerged aerobic conditions in an aqueous carbohydrate medium, containing a nitrogen nutrient, said conditions being conducted at a pH of about 7, which are sufficient to biotransform FR-900520.

The resultant Compound I exhibits FK-506 immunosuppressant activity, i.e., positive inhibition of T-cell activation, as demonstrated by the calcium ionophore (ionomycin) plus phorbol myristate acetate (PMA) induced T-cell stimulation assay, also referred to herein as the "T-cell proliferation assay".

The principle of this assay is to measure the proliferation of mouse T lumphocytes stimulated with the combination of ionomycin plus PMA. A positive sample e.g. FK-506, in this assay will inhibit T-cell proliferation, as indicated by reduced tritiated thymidine uptake.

In accordance with this invention, there is provided a process for producing a new FK-506 immunosuppressant, identified as Compound I, comprising the step of culturing a strain of Actinomycete, MA6963, ATCC No. 55230, together with FR-900520 under submerged aerobic fermentation conditions in an aqueous carbohydrate medium, containing a nitrogen nutrient, for a sufficient time to produce product Compound I.

Figure 1:
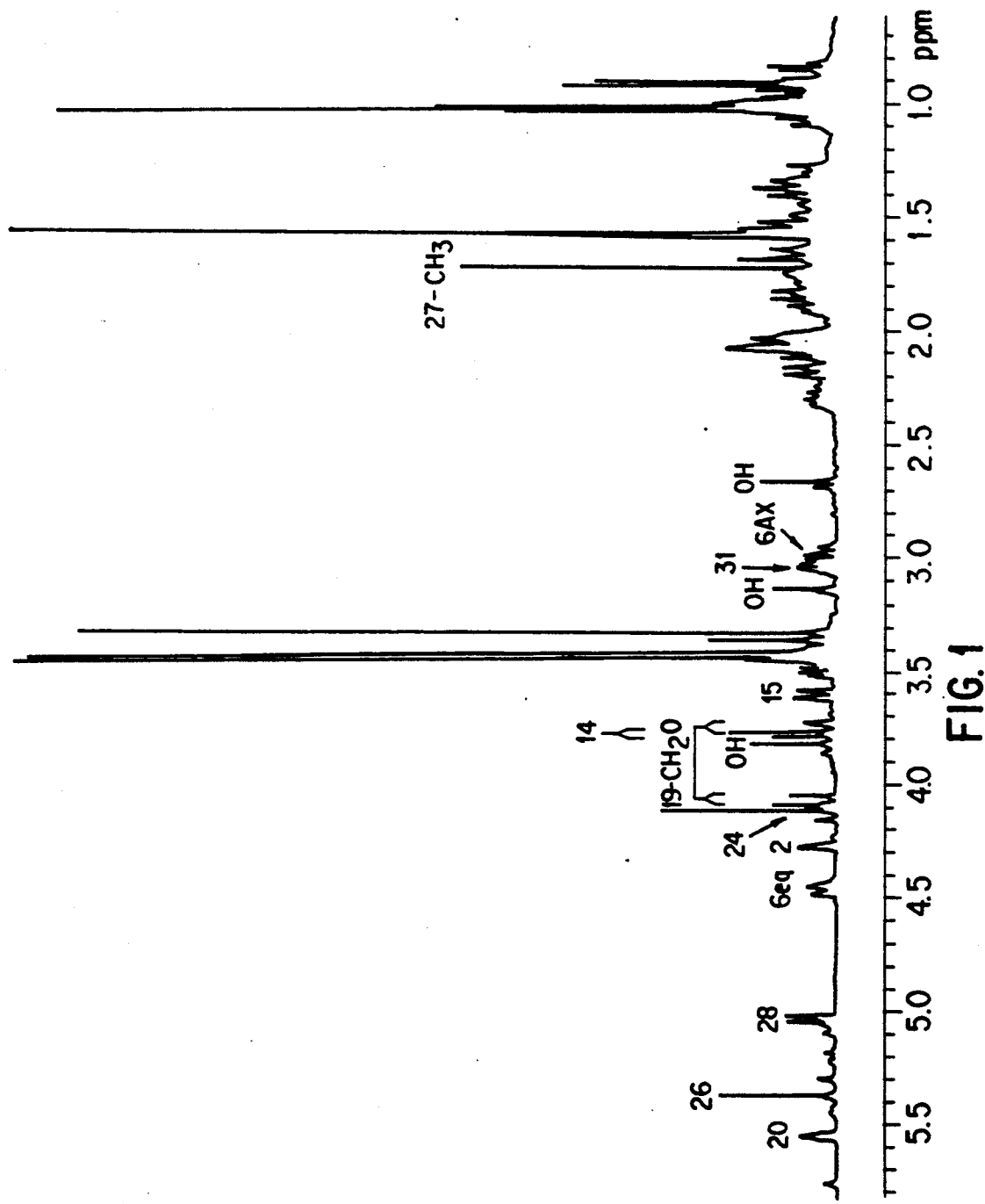
FIG. 1 is an $^1$H nuclear magnetic resonance (NMR) spectrum taken at 400 MHz of Compound I in CDCl$_3$.
Figure 2:
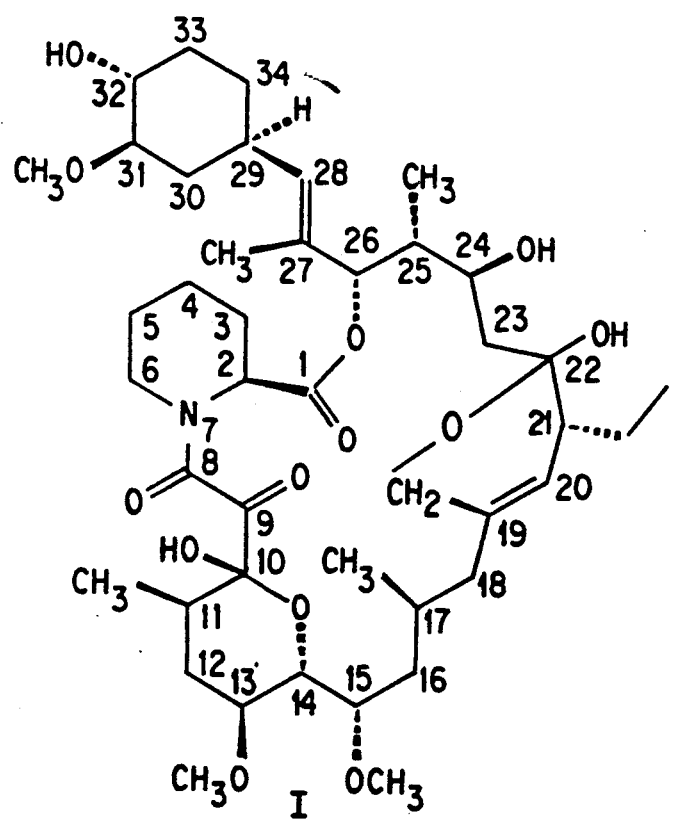
FIG. 2 illustrates the assigned molecular structure of the compound.

Further provided is a new FK-506 immunosuppressant, Compound I, produced by the above process which exhibits positive inhibition of T-cell activation by the T-cell proliferation assay and exhibits a proton nuclear magnetic resonance spectrum illustrated in FIG. 1 and has an assigned structural formula as also identified in FIG. 1.

Also provided is a pharmaceutical composition containing a therapeutically effective amount of Compound I in combination with a pharmaceutically acceptable, substantially non-toxic carrier or excipient.

In addition, there is provided a method of use for treating human host to prevent transplantation rejection, or for treating autoimmune disease or infectious disease comprising administering to said host a therapeutically effective amount of Compound I.

Furthermore there is provided a Compound I ally pure culture of Actinomycete, (MA6963), ATCC No. 55230.

DETAILED DESCRIPTION OF THE INVENTION AND PREFERRED EMBODIMENTS

The present invention involves the fermentation of Actinomycete, MA6963, ATCC No. 55230, together with FR-900520 to produce Compound I. The microorganism is currently on deposit with the American Type Culture Collection, 12301 Parklawn Drive in Rockville, Maryland as ATCC No. 55230, and in the Merck Culture Collection in Rahway, New Jersey as MA6963. The physical characteristics and taxonomy, including morphological, cultural, biological and physiological characteristics are briefly described hereinbelow.

The following is a general description of *Streptomyces lavendulae* strain MA6963. Observations of growth, general cultural characteristics and carbon source utilization were made in accordance with the methods of Shirling and Gottleib (Internat. J. System Bacteriol. 16:313–340). Chemical composition of the cells was determined using the method of Lechevalier and Lechevalier (in Actinomycete Taxonomy, A. Dietz and D. W. Thayer, Ed. Society for Industrial Microbiology, 1980). Whole cell fatty acids were derivatized and analyzed as methyl esters (FAMEs) by gas chromatography by the procedure of Miller and Berger using a MIDI Microbial Identification System (Microbial Identification Systems, Newark Delaware). Coloration of the culture was determined by comparison with color standards contained in the Inter-Society color council-National Bureau of Standards Centroid Color Charts (U.S. Dept. of Commerce National Bureau of Standards supplement to NBS circular 553, 1985).

Source—This culture was isolated from a soil sample collected in Morris County, N.J.

Analysis of Cell Wall Composition—Peptidoglycan contains LL-diaminopimelic acid.

General growth characteristics—Good growth on yeast malt extract agar (YME), glycerol asparagine agar, inorganic salt starch agar, oatmeal, trypticase soy agar and peptone iron agar. Fair growth on Czapek's agar and tap water agar supplemented with NZ-amine (Shefield Chemical Co.) Culture also grows in tryptone yeast extract broth. Culture grows at 27° C. and 37° C.

Colony morphology—(on YME at 21 d) Substrate mycelium is medium brown with yellow brown edges. Aerial mycelium white. Spore mass is abundant and pinkish white in color. Colonies are opaque, raised and have entire edges, rubbery in consistency with a matte surface texture.

Micromorphology—Aerial mycelia (0.57 μm) arise from substrate mycelia and are branched, long and slightly flexous. In mature cultures (7-28 d p.i.) the aerial mycelium terminates in flexous chains of spores that occasionally terminate in hooks, loops or open spirals (1-2 turns). This characteristic is especially noticeable in areas of dense aerial development. Sporulation occurs on YME, inorganic salts-starch agar, oatmeal, glycerol asparagine agar, tap water agar with NZ-amine and Czapek's agar. On YME knot-like structures are observed at the junction of hyphae. On inorganic salts-starch agar dark chromatic granules are observed.

Miscellaneous physiological reactions—Culture produces $H_2S$ in peptone-iron agar. Melanoid pigments are formed in TY broth and on peptone iron agar slants. A dark gray diffusible pigment is formed on inorganic salts-starch agar. Starch is weakly hydrolyzed. Carbon source utilization pattern is as follows: good utilization of celloboise, D-mannose; moderate utilization of D-fructose, α-D-glucose, D-maltose; poor utilization of α-D-lactose, β-D-lactose; no utilization of L-arabinose, D-arabinose, inositol, D-mannitol, D-raffinose, L-rhamnose, sucrose, D-xylose, L-xylose. Cellular Fatty Acid Analysis—Gas chromatography of FAMEs, prepared from cultures grown on trypticase-soy broth agar (BBL) for 4 d at 27° C. revealed that the major fatty acids of this strain were: 15:0 anteiso (30.8-32.6%), 16:0 iso (21.7-22.0%), 17:0 anteiso (6.0-6.7%), 15:0 iso (7.2-7.4%), 16:0 anteiso (5.9-6.6%), 14:0 sio (4.6-5.6%), 17:0 cyclopropane (4.0-4.6%), 17:1 anteiso C (3.2%), 16:1 cis 9 (2.9-3.0%) and 16:1 iso H (2.6-2.7%). Other fatty acids present occurred at levels <2.5%.

Diagnosis—Cell wall analysis reveals that MA6963 has a type I cell wall. Morphological studies reveal that the culture produces long chains of spores on flexous sporophores that terminate in loops, hooks or extended spirals. Sporophores arise from the aerial mycelium. These are characteristics typical for strains of Streptomyces. A comparison of the phenotypic data of MA6963 with that of the validly published species of Streptomyces in the taxonomic literature (accompanying references 1-8) shows that this strain bears a strong resemblance to *Streptomyces columbiensis*, *Streptomyces flavotricini*, *Streptomyces lavendulae*, and *Streptomyces virginiae*. *Streptomyces flavotricini*, *Streptomyces columbiensis*, and *Streptomyces virginiae* are currently considered subjective synonyms of *Streptomyces lavendulae*. It differs from the type material of these species on the characteristics: production of soluble pigments, elaboration of knot-like structures in the aerial mycelium and the production of chromatic granules. Cluster analysis of the FAME profile of MA6963 against the MIDI actinomycete library (ACTINI [Rev 1.0]) as well as our own actinomycete library indicate a fatty acid composition consistent with *Streptomyces lavendulae*. Based upon these results, MA6963 is considered a new strain of *Streptomyces lavendulae*.

Bibliography

1. Shirling, E. B. and Gottlieb, D., Int. J. System. Bacteriol. 18:69 (1968)
2. Shirling, E. G. and Gottlieb, D., Int. J. System. Bacteriol. 18:279 (1968)
3. Shirling, E. B. and Gottlieb, D., Int. J. System. Bacteriol. 19:391 (1969)
4. Shirling, E. G. and Gottlieb, D., Int. J. System. Bacteriol. 22:265 (1972)
5. Nonomura, H. J. Ferment. Technol. 52:78 (1974)
6. Pridham, T. and Tresner, H., in Bergey's Manual of Determinative Bacteriology, Eighth Edition, R. E. Buchanan and N. E. Gibbons, Ed., Williams and Wilkins, Baltimore (1974)
7. Loci, R. in Bergey's Manual of Systematic Bacteriology, Vol 4., St. Williams, M. E. Sharpe and J. G. Holt. Ed., Williams and Wilkins, Baltimore (1989)
8. Miller, L., and T. Berger Hewlett-Packard Application Note 228-41. Hewlett-Packard Co. Avondale, Pa.

| Carbohydrate utilization pattern of Streptomyces sp. MA6963 at 21 days | |
|---|---|
| Carbon source | Utilization |
| D-arabinose | 0 |
| L-arabinose | 0 |
| cellobiose | 3 |
| D-fructose | 2 |
| inositol | 0 |
| α-D-lactose | 1 |
| β-D-lactose | 1 |
| D-maltose | 2 |
| D-mannitol | 0 |
| D-mannose | 3 |
| D-raffinose | 0 |
| L-rhamnose | 0 |
| sucrose | 0 |
| D-xylose | 0 |
| L-xylose | 0 |
| a-D-glucose (control) | 2 |

3 = good utilization
2 = moderate utilization
1 = poor utilization
0 = no utilization

| Medium | Amount of Growth MA6963 | Cultural characteristics of MA6963 at 21 days Aerial Mycelium MA6963 | Soluble Pigments | Reverse Color |
|---|---|---|---|---|
| Yeast Extract Malt Extract | good | Aerial mycelium pinkish white (9 pk.White). Spores borne in slightly | brown | Medium brown (58 m.Br) |

-continued

| Medium | Amount of Growth MA6963 | Cultural characteristics of MA6963 at 21 days | | |
|---|---|---|---|---|
| | | Aerial Mycelium MA6963 | Soluble Pigments | Reverse Color |
| Glucose Asparagine | good | flexous chains with knots, some short open spirals. Aerial mycelium pale pink (7 p.Pink). Spores borne in slightly flexous chains with short open spirals. | none noted | Pale orange yellow (73 p.OY) |
| Inorganic Salts Starch | good | Aerial mycelium pinkish gray (10 pk.Gray). Spores borne in tightly coiled spirals. Starch weakly hydrolyzed. Black patches with chromatic granules observed. | dark gray | Black (267 Black) |
| Oatmeal | good | Aerial mycelium pale pink (7 p.Pink). Spores borne in slightly flexous chains with short open spirals. | none noted | Light yellow brown (76 l.y Br) |
| Sigma Water | very sparse | No aerial mass observed | none noted | Yellow white (92 yWhite) |
| Czpak | sparse | Aerial mycelium yellow white (92 y.White). Spores borne in short spirals, loops and hooks. | none noted | Transparent |
| Peptone Iron | good | | Melanin positive, H$_2$S positive. | |

The present invention process can be practiced with any Compound I producing strain of Actinomycete, and particularly preferred is the ATCC No. 55230 strain (MA6963).

In general, Compound I can be produced by culturing the MS6963 strain, in an aqueous nutrient medium containing sources of assimilable carbon and nitrogen, preferably under submerged aerobic conditions (e.g. shaking culture, submerged culture, etc.). The aqueous medium is preferably maintained at a pH of about 7 at the initiation and termination (harvest) of the fermentation process. A higher pH leads to substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described herinbelow.

The preferred sources of carbon in the nutrient medium are carbohydrates such as glucose, xylose, galactose, glycerin, starch, dextrin, and the like. Other sources which may be included are maltose, raffinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, polypropylene glycol, mineral oil or silicone may be added.

The FR-900520 starting material (also referred to in the art as "FK-520") can be obtained by the fermentation of S. hygroscopicus var. ascomyceticus, ATCC No. 14891, as described in U.S. Pat. No. 3,244,592, and by the fermentation of S. hygroscopicus subsp. yakushimaensis No. 7278, to produce FR-900520, as described in EPO Publication No. 0184162 to Fujisawa, and U.S. Pat. No. 4,894,366.

As to the conditions for the production of Compound I in massive amounts, submerged aerobic cultural conditions are preferred therefore. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of Compound I. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of Compound I and is generally autoclaved to sterilize the medium prior to inoculation. The pH of the medium is generally adjusted to about 7.0 prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°-35° C., for a period of about 10 hours to 20 hours, which may be varied according to fermentation conditions and scales. Preferably, the production cultures are incubated for about 17 hours at 27° C. on a rotary shaker operating at 220 rpm, wherein the pH of the fermentation medium is maintained at 7.0 to harvest.

Preferred culturing/production media for carrying out the fermentation include the following media:

|  | g/liter |
| --- | --- |
| Seed Medium | |
| Dextrose | 1.0 |
| Dextrin | 10.0 |
| Beef Extract | 3.0 |
| Ardamine pH | 5.0 |
| NZ Amine Type E | 5.0 |
| MgSO$_4$.7H$_2$O | 0.05 |
| K$_2$HPO$_4$ | 0.37 |
| Adjust pH to 7.1 | |
| Add CaCO$_3$ 0.5 g/l | |
| Transformation Medium B | |
| Glucose | 20 |
| Soya Meal | 5 |
| Yeast Autolysate | 5 |
| Nacl | 5 |
| MES | 9.8 |
| Adjust pH to 7.0 | |

The produced Compound I can be recovered from the culture medium by conventional means which are commonly used for the recovery of other known biologically active substances. The Compound I substance produced is found in the cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred method is solvent extraction, particularly using methanol.

The product Compound I from the fermentation exhibits antagonist activity versus the FK-506 immunosuppressive activity by the "T-cell proliferation assay" and possesses utility on this basis and exhibits the following physical characteristics:
1. White amorphous powder
2. Solubility in methanol
3. Molecular weight of 807, as determined by FAB mass spectroscopy which is consistent with the assigned structure in FIG. 1.

The Compound I obtained according to the fermentation processes as explained above can beisolated and purified in a conventional manner, for example, extraction, precipitation, fractional crystallization, recrystallization, chromatography, and the like.

It is to be noted that in the aforementioned fermentation reactions and the post-treatment of the fermentation mixture therein, the conformer and/or stereo isomer(s) of Compound I due to asymmetric carbon atom(s) or double bond(s) of the Compound I may occasionally be transformed into the other conformer and/or stereoisomer(s), and such cases are also included within the scope of the present invention.

The Compound I of the present invention possesses antagonist pharmacological activity therefore is useful or an antidote versus FK-506 for inadvertent or accidental overdosage of FK-506 in a Therapeutic program involving FK-506 designed for the treatment and prevention of the transplantation rejection of organs or tissues such as heart, kidney, liver, medulla ossium, skin, etc., graft-versus-host diseases by medulla ossium transplantation, autoimmune diseases such as rheumatoid arthritis, systemic lupul erythematosus, Hashimoto's thyroiditis, multiple sclerosis, myasthenia gravis, type I diabetes, uveitis, and the like.

The pharmaceutical composition of this invention can be used in the form of a pharmaceutical preparation, for example, in solid, semisolid or liquid form, which contains the Compound I, of the present invention, as an active ingredient, in admixture with an organic or inorganic carrier orexcipient suitable for external, enteral or parenteral applications. The active ingredient may be compounded, for example, with the usual nontoxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of diseases.

For applying this composition to a human, it is preferably to apply it by parenteral or enteral administration. While the dosage of therapeutically effective amount of the Compound I, varies from, and also depends upon the age and condition of each individual patient to be treated, and the amount of FK-506 administered, which should be equal to the amount of FK-506 overdosage and greater, a daily dose (calculated on the basis of a 70 kg man) of about 0.01-1000 mg, preferably 0.1-500 mg and more preferably 0.5-100 mg, of the active ingredient is generally given for treating diseases, and an average single dose of about 0.5 mg, 1 mg, 5 mg, 10 mg, 50 mg, 100 mg, 250 mg and 500 mg is generally administered.

The following examples are given for the purpose of illustrating the present invention and should not be construed as being limitations on the scope or spirit of the instant invention.

EXAMPLE 1

Microorganism and Culture Conditions

A frozen vial (2.0 ml) of culture MA6963, ATCC No. 55230, was used to inoculate a 250 ml baffled shake flask containing 50 ml of an autoclaved (sterilized) seed medium consisting of (in units of grams/liter) dextrin 10.0, dextrose 1.0, beef extract 3.0, ardamine PH (Yeast Products, Inc.) 5.0, N-Z Amine type E 5.0, MgSO$_4$.7H$_2$O 0.05, KH$_2$PO$_4$ 0.3, and CaCO$_3$ 0.5. The pH of the seed medium was adjusted to 7.1 before autoclaving. The seed was incubated in the seed medium at 27° C. for 24 hours on a rotary shaker operating at 220 rpm. A 2.5 ml aliquot of the resulting seed medium was used to inoculate a 250 ml non-baffled shake flask containing 50 ml of the following previously autoclaved (sterilized) fermentation medium:

| Soy-Glucose Medium | |
| --- | --- |
| Glucose | 20.0 |
| Soya Meal | 5.0 |
| Yeast Autolysate | 5.0 |
| NaCl | 5.0 |
| MES | 9.8 |
| Adjust pH to 7.0 | |

FR-900520 (also known as FK-520) was added as a solution in dimethylsulfoxide to achieve a final concentration of 0.05 mg/ml concentration. The shake flask contents were subsequently incubated for 48 hrs. at 27° C. on a rotary shaker operating at 220 rpm.

Isolation and Purification

The whole broth (1000 ml) was extracted three times with methylene chloride (3×500 ml). Methylene chloride extracts were combined, dried over sodium sulfate, and concentrated under vacuum to an oily residue. The residue was dissolved in methanol and subjected to high performance liquid chromatography (HPLC). HPLC was carried out on Whatman Magnum 9 Partixil 10 ODS-3 Column (9.6 mm ID×25 cm) at room temperature and monitored at 205 nm. The column was developed at 4 ml/min with a linear gradient of 40% to 80% acetonitrile in 0.1% phosphoric acid. The fraction with a retention time of 22.4 minutes (Compound I) was pooled, adjusted to pH 4.0, evaporated to remove acetonitrile, and desalted using a C18 Sep Pak (Waters Associate) by elution with methanol to yield, 6.8 mg of Compound I after evaporation to dryness.

ANALYTICAL SPECTRAL DATA

Mass spectral data of the subject Compound I biotransformation product obtained by the incubation of FR-900520 with culture MA 6963, coupled with the proton NMR data, as shown in the spectrum of FIG. 1, is consistent with the following assigned molecular structure(Compound I), which is also shown in FIG. 1:

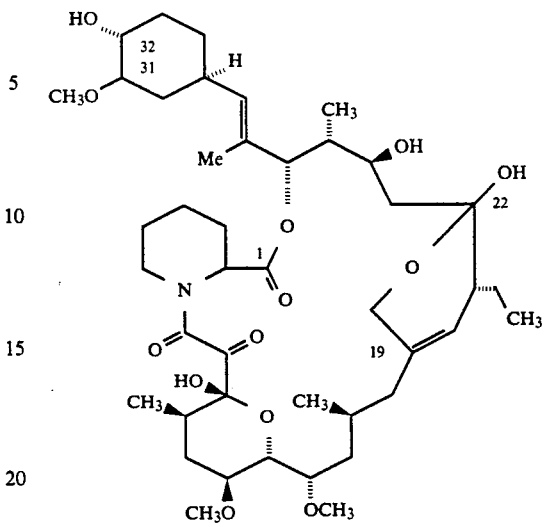

EXAMPLE 2

T-Cell Proliferation Assay

1. Sample Preparation

Purified Compound I, as prepared by HPLC above, was dissolved in absolute ethanol at 1 mg/ml.

2. Assay

Spleens from C57Bl/6 mice were taken under sterile conditions and gently dissociated in ice-cold RPMI 1640 culture medium (GIBCO, Grand Island, N.Y.) supplemented with 10% heat-inactivated fetal calf serum (GIBCO). Cells were pelleted by centrifugation at 1500 rpm for 8 minutes. Contaminating red cells were removed by treating the pellet with ammonium chloride lysing buffer (GIBCO) for 2 minutes at 4° C. Cold medium was added and cells were again centrifuged at 1500 rpm for 8 minutes. T lumphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 250° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hours. Non-adherent T lymphocytes were eluted fromthe columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$ M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The control, being the medium without test drug, and various below-indicated dilutions of the sample (above-described purified Compound I to be tested were then added in triplicate wells at 20 μl/well. FR-900506 was used as a standard. The culture plates were then incubated at 37° C. in a humidified atmosphere of 5% $CO_2$ 95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting method (Betacounter). Mean counts per minute of replicate wells were calculated and the results expressed as percent inhibition of tritiated thymidine uptake (proliferation) as follows:

$$\% \text{ Inhibition} = 100 - \left[ \frac{\text{Mean cpm sample tested}}{\text{Mean cpm control medium}} \times 100 \right].$$

The results of % inhibition at various concentrations of Compound I are presented in the following Table:

TABLE

Effects of Compound I on the proliferative response of Splenic T-cells stimulated with ionomycin + PMA

| Sample | Concentration of Compound I (nM) | Percent of Inhibition |
|---|---|---|
| | 50.0 | 94 |
| | 25.0 | 94 |
| | 12.5 | 91 |
| | 6.2 | 78 |
| | 3.1 | 55 |
| | 1.6 | 19 |
| | 0.8 | 16 |

Notes:
1. Mouse T cell cultures were pulsed with $^3$H-thymidine for 4 hours prior to harvesting at 48 hours.
2. Standard FR-900506 (10 ng/ml) gave 99% inhibition.
3. $IC_{50}$ = 3.17 ng/ml = 3.9 nM, for Compound I, and generally in the range of 1.57 to $5.20 \times 10^{-9}$ molar. This is based on a series of 5 additional experiments giving $IC_{50}$ (ng/ml) values of 1.57, 1.92, 5.20, 4.80, 4.50. The mean $IC_{50}$ for all of 6 above runs is 3.52 ± 1.4 (SEM) and 4.36 ± 1.7 nM.
4. Inhibition of T-Cell proliferation by Compound I was reversed by the addition of 50 units/ml of IL-2 (recombinant IL-2) at the initiation of culture.

What is claimed is:
1. A biologically pure culture of (MA6963), ATCC No. 55230 *Streptomyces lavendulae*.

* * * * *